United States Patent
Dubois

(10) Patent No.: US 8,143,454 B2
(45) Date of Patent: Mar. 27, 2012

(54) METHOD FOR SYNTHESIS OF ACROLEIN FROM GLYCEROL

(75) Inventor: Jean-Luc Dubois, Millery (FR)

(73) Assignee: Arkema France, Colombes (FR)

( * ) Notice: Subject to any disclaimer, the term of this patent is extended or adjusted under 35 U.S.C. 154(b) by 173 days.

(21) Appl. No.: 12/808,261

(22) PCT Filed: Dec. 16, 2008

(86) PCT No.: PCT/FR2008/052314
§ 371 (c)(1), (2), (4) Date: Jun. 15, 2010

(87) PCT Pub. No.: WO2009/081021
PCT Pub. Date: Jul. 2, 2009

(65) Prior Publication Data
US 2010/0274038 A1    Oct. 28, 2010

(30) Foreign Application Priority Data
Dec. 20, 2007 (FR) .................... 07 60075

(51) Int. Cl.
*C07C 45/51* (2006.01)
*C07C 45/56* (2006.01)

(52) U.S. Cl. ............ 568/465; 568/468
(58) Field of Classification Search ........ 568/465, 568/468
See application file for complete search history.

(56) References Cited

U.S. PATENT DOCUMENTS

| | | |
|---|---|---|
| 4,851,583 A | 7/1989 | Bockowski et al. |
| 5,079,266 A | 1/1992 | Bockowski et al. |
| 5,216,179 A | 6/1993 | Hoepp et al. |
| 5,387,720 A | 2/1995 | Neher et al. |
| 7,396,962 B1 | 7/2008 | Dubois et al. |
| 7,655,818 B2 | 2/2010 | Dubois et al. |
| 2008/0146852 A1 | 6/2008 | Dubois et al. |
| 2009/0068440 A1 | 3/2009 | Bub et al. |

FOREIGN PATENT DOCUMENTS

| | | |
|---|---|---|
| FR | 695931 | 12/1930 |
| FR | 2913974 | 9/2008 |

*Primary Examiner* — Sikarl Witherspoon
(74) *Attorney, Agent, or Firm* — Steven D. Boyd

(57) ABSTRACT

The invention provides a technology for producing acrolein from glycerol while maintaining high reagent partial pressures, which leads to higher yield. The invention more particularly relates to a method for producing acrolein from glycerol that comprises the intermediate step of forming glycerol and acrolein cyclic acetals.

10 Claims, 1 Drawing Sheet

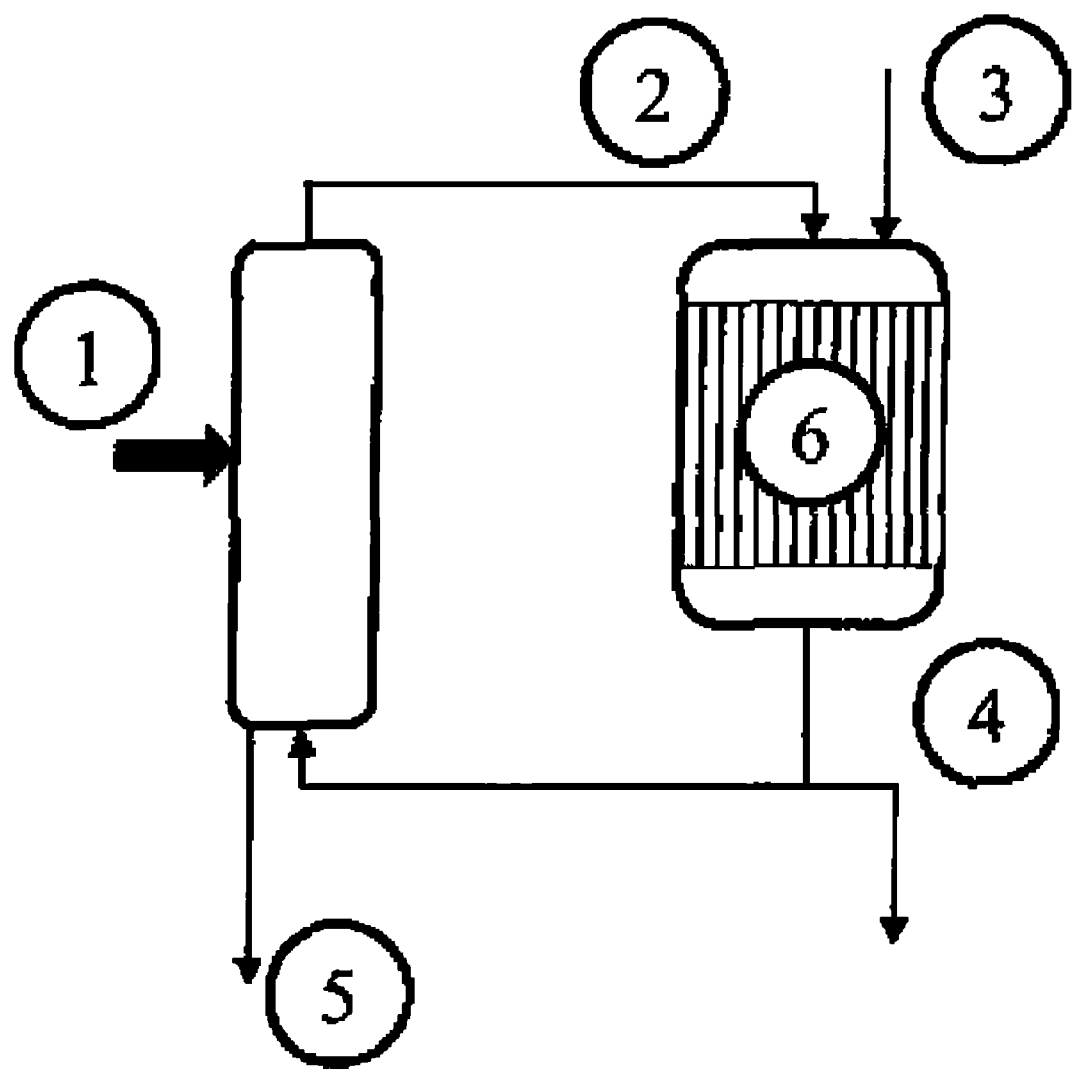

METHOD FOR SYNTHESIS OF ACROLEIN FROM GLYCEROL

FIELD OF THE INVENTION

The present invention relates to a method for producing acrolein from glycerol, comprising an intermediate step of forming cyclic acrolein glycerol acetals.

BACKGROUND OF THE INVENTION

Glycerol, derived from the methanolysis of plant oils at the same time as methyl esters, constitutes a renewable starting material which meets the criteria associated with the new concept of "green chemistry".

It has been known for a long time that glycerol can lead to the obtaining of acrolein according to the following dehydration reaction:

$CH_2OH-CHOH-CH_2OH \Leftrightarrow CH_2=CH-CHO + 2H_2O$

As a general rule, in order to obtain acrolein, it is necessary to use a sufficient temperature, and/or partial vacuum to shift the reaction. The reaction can be carried out in a liquid phase or in a gas phase and it is generally catalyzed by acids.

Various methods for producing acrolein from glycerol have been the subject of patent applications; reference may in particular be made to documents FR 695931; U.S. Pat. No. 5,387,720; WO 06/087083; WO 06/087084; WO 06/136336.

The glycerol is generally used in the form of aqueous solutions, which are more economical. However, the glycerol solution should not be too dilute owing to the energy cost generated by the evaporation of the aqueous solution of glycerol.

In methods for dehydrating glycerol so as to give acrolein in the gas phase, it is necessary to evaporate the glycerol at a high temperature, generally above 220° C. It is, however, well known that glycerol is not stable at high temperature, in particular at above 220° C.

In the methods proposed for evaporating aqueous solutions of glycerol, it is therefore very critical to control the temperature since certain undesirable reactions can take place, such as the formation of nitrogenous compounds by degradation of protein material present in the crude glycerol, or the formation of glycerol ethers or of polyglycerol. It is therefore important to limit the residence time of the glycerol at high temperature, and also this temperature.

The solution conventionally developed is to use a low glycerol partial pressure, for example with glycerol solutions that are sufficiently diluted in water, or at reduced pressure, in order to decrease the temperature necessary for evaporation of the glycerol. However, this type of solution results in low yields since the partial reactive pressure is necessarily low.

The methods for evaporation conventionally used do not therefore make it possible to have high glycerol partial pressures in the vapor phase. Moreover, it is often necessary to combine the glycerol evaporation step with a pretreatment for eliminating impurities, such as sodium chloride, sodium sulfate, non-glycerin organic matter, or methanol, that may be present in the aqueous solution of glycerol.

In patent application FR 2 913 974, the applicant company describes a single-step method for vaporizing an aqueous glycerol solution and simultaneously eliminating the impurities present in the solution or generated during the evaporation. This method consists in vaporizing the aqueous glycerol solution in contact with a fluidized bed containing an inert solid maintained at a temperature sufficient to allow instantaneous vaporization of the glycerol and of the water. The impurities present in the aqueous solution are simultaneously eliminated since the fluidized bed technique makes it possible to continuously withdraw part of the solid in order to regenerate it ex-situ. The glycerol vapors obtained according to this method can then be used directly in a method for producing acrolein in the gas phase.

However, this prior glycerol vaporization step can prove to be expensive if the glycerol is used in the form of a dilute aqueous solution.

SUMMARY OF THE INVENTION

Thus, an objective of the present invention consists in providing a technology for producing acrolein from glycerol which makes it possible to maintain high reactant partial pressures, resulting in a high yield.

Even more advantages will become apparent during the description of the present invention which follows.

It has been discovered, entirely surprisingly, that it is possible to produce acrolein without the abovementioned drawbacks by passing a cyclic acrolein glycerol acetal over a catalyst conventionally used for the dehydration of glycerol, the acetal being prepared beforehand from an aqueous solution of glycerol and acrolein.

Documents U.S. Pat. No. 4,851,583 and U.S. Pat. No. 5,079,266 describe a method for generating acrolein by de-acetalization of a cyclic acrolein glycerol acetal in contact with a non-siliceous catalyst, the advantage of such a method lying in the fact that the reaction is carried out at ambient temperature.

BRIEF DESCRIPTION OF THE DRAWINGS

FIG. 1 is a schematic of a process in accordance with the present invention.

DETAILED DESCRIPTION OF THE INVENTION

In the context of the present invention, the desired effect is that of being able to more readily vaporize the glycerol at a lower temperature, with its concentration being limited during the vaporization step.

This effect is obtained with the cyclic acrolein glycerol acetals.

This is because the cyclic acetals derived from glycerol and from acrolein, corresponding to formulae (I) and (II):

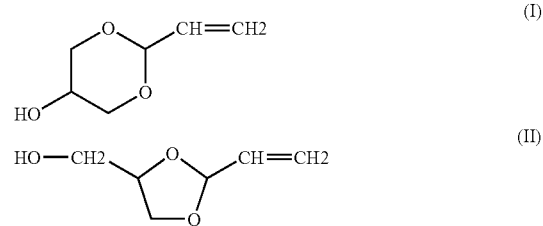

have boiling points that are lower than that of glycerol, respectively 209° C.±35° C. and 185° C.±25° C. (values calculated by the ACD/labs software) compared with 290° C. for glycerol.

It has been possible to demonstrate that these acetals react on contact with a solid acid catalyst having a Hammett acidity of less than +2, thus releasing not only acrolein, but also glycerol which, according to the dehydration reaction, also leads to acrolein.

The subject of the present invention is therefore a method for producing acrolein from glycerol, comprising the following steps:

(a) in a first reactor, an aqueous glycerol solution is reacted with acrolein in the presence of an acid catalyst so as to form cyclic acrolein glycerol acetals,
(b) the stream derived from step (a) is evaporated at a temperature of between 100° C. and 300° C.,
(c) the gas stream previously obtained is sent over a glycerol dehydration catalyst in a second reactor, so as to produce acrolein,
(d) the acrolein produced is separated from the stream derived from step (c), a part of the acrolein being recycled to the unit for production of acetals of step (a).

The method according to the invention is particularly suitable for the continuous production of acrolein by dehydration of glycerol, by means of the cyclic acetals thereof.

Other characteristics and advantages of the invention will emerge more clearly on reading the description which follows with reference to the attached single FIGURE, which is in no way limiting.

According to the method of the invention, step (a) consists in bringing a stream of an aqueous glycerol solution 1, having, as a general rule, a concentration of at least 20% by weight, into contact with acrolein, in a first reactor in the presence of an optionally solid, acid catalyst. Preferably, an aqueous glycerol solution having a concentration ranging from 20% to 80% by weight is used.

The production of cyclic acrolein glycerol acetals in the presence of a solid acid catalyst has been known for many years. Reference may in particular be made to the operating conditions described in U.S. Pat. No. 5,216,179, which describes a method for producing mixtures of cyclic acrolein glycerol acetals by reacting acrolein and glycerol in the presence of an acid catalyst, more particularly in the presence of strongly acidic ion exchange resins, preferably containing sulfonate groups.

The reaction can be carried out within a wide temperature range, from 0° C. to 150° C., preferably from 20° C. to 100° C., in the presence of the reaction mixture as solvent, which is essentially made up of the mixture of cyclic acrolein glycerol acetals and of the water of the reaction or originating from the aqueous glycerol solution. The reaction mixture necessary at the start for carrying out the first step of the method according to the invention may be produced in any other way, in particular by means of mixing the components. Many prior art catalysts may be suitable as solid acid catalyst for carrying out step (a); preferably, acidic resins are used.

As an option, the cyclic acetal production unit can be supplied with an aqueous solution of crude glycerol (glycerin), i.e. containing impurities and in particular salts (NaCl or $Na_2SO_4$). In this case, the acetalization catalyst is preferably a homogeneous catalyst which is soluble in the aqueous phase. A salt-enriched concentrate is then removed from the acetal production unit at 5. This concentrate can then be processed so as to remove all or part of the salts, and the glycerol is recycled to the acetal production unit (not represented in the FIGURE).

In step (a) of the method according to the invention, it is not necessary to obtain total conversion of the glycerol, the unconverted glycerol and/or unconverted acrolein then being sent to the dehydration reactor 6, and the desired effect being essentially that of being able to more readily vaporize the glycerol at a lower temperature, with its concentration being limited during the vaporization step. As a general rule, a glycerol conversion rate of 50% is sufficient and the reaction is generally carried out so as to achieve a conversion rate ranging from 50% to 80%. The acetalization reaction is carried out with an acrolein/glycerol molar ratio in general ranging from 0.5 to 5, preferably from 0.5 to 2.5.

According to the method of the invention, in a second step (b), the stream 2 derived from the first step (a) is vaporized, this stream comprising a mixture of the cyclic acetals, the water derived from the acetalization reaction, the water present in the solution of glycerol and/or acrolein, but also acrolein and/or glycerol having not reacted during step (a). The evaporation temperature is below the decomposition temperature of glycerol, which limits not only the energy consumption but also the loss of yield owing to glycerol degradation. The evaporation temperature is generally between 100° C. and 300° C., preferably between 130° C. and 250° C., and more preferably between 150° C. and 220° C. For this step (not represented in the FIGURE), any type of evaporator available in the prior art can be used, in particular the equipment described in Techniques de l'Ingénieur, Genie des Procédés [Techniques of the engineer, process engineering], J 2-320 pages 1-27, for instance jacketed or coil evaporators, steam-heated tube evaporators, crystallization evaporators, falling film evaporators, forced circulation evaporators, agitated film evaporators, plate-type evaporators, multistage expansion evaporators, or specialized heating evaporators. An evaporator suitable for solutions with a high viscosity, or at risk of salt crystallization, is advantageously used, for example an agitated film evaporator, a forced circulation evaporator, or a falling film evaporator.

For this step, the fluidized bed evaporation technique as described in patent application FR 07.53896 can also be used.

The stream 2 derived from the reaction (a) is continuously drawn off from the first reactor. The pH of this stream can optionally be adjusted to between 4 and 7 using a buffer solution or an anionic resin, before being subjected to the vaporization step (b). The objective of this is to limit the decomposition of the cyclic acetals during the subsequent vaporization step; however, it is not essential to control the pH.

The stream 2 derived from the reaction (a) can also optionally be diluted with water so as to bring the mixture to the proportions necessary for the subsequent dehydration reaction.

Surprisingly, it has been noted that the presence of water in the reaction stream during the dehydration reaction improves the acrolein selectivity, limiting the formation of by-products.

In a third step (c) according to the method of the invention, the gas stream derived from step (b), containing the mixture of cyclic acetals, steam and, optionally, unreacted glycerol and/or unreacted acrolein and by-products, is directed to a reactor 6 containing a glycerol dehydration catalyst. The reactor 6 may be a fixed bed, fluidized-bed or circulating fluidized-bed adiabatic reactor, a multitube fixed-bed reactor, or a plate exchanger reactor.

The dehydration catalyst in reactor 6 is a solid acid catalyst. The catalysts which are suitable are homogeneous or multiphase materials which are insoluble in the reaction medium and which have a Hammett acidity, denoted $H_0$, of less than +2. As indicated in U.S. Pat. No. 5,387,720, which refers to the article by K. Tanabe et al., in "Studies in Surface Science and Catalysis", vol. 51, 1989, chap 1 and 2, the Hammett acidity is determined by amine titration using indicators or by adsorption of a base in the gas phase. The catalysts that meet the requirement of $H_0$ acidity of less than +2 can be chosen from natural or synthetic siliceous materials or acidic zeolites; inorganic supports, such as oxides, coated with inorganic acids, mono-, di-, tri- or polyacids; oxides or mixed oxides or also heteropolyacids.

These catalysts may be made up of a heteropolyacid salt in which protons of said heteropolyacid are exchanged with at least one cation chosen from the elements belonging to groups I to XVI of the Periodic Table of Elements, these heteropolyacid salts containing at least one element chosen from the group comprising W, Mo and V.

Advantageously, the catalysts are chosen from zeolites, Nafion® composites (based on sulfonic acid-bonded fluoropolymers) available for E.I. DuPont de Nemours and Company, chlorinated aluminas, the acids and salts of phosphotungstic acids and/or silicotungstic acids, and various solids of metal oxide type, such as tantalum oxide $Ta_2O_5$, niobium oxide $Nb_2O_5$, alumina $Al_2O_3$, titanium dioxide $TiO_2$, zirconia $ZrO_2$, tin oxide $SnO_2$, silica $SiO_2$ or silico-aluminate $SiO_2$—$Al_2O_3$, impregnated with acid functions such as borate $BO_3$, sulfate $SO_4$, tungstate $WO_3$, phosphate $PO_4$, silicate $SiO_2$ or molybdate $MoO_3$. According to the data in the literature, these catalysts all have a Hammett acidity $H_0$ of less than +2.

The preferred catalysts are sulfated zirconias, phosphated zirconias, tungstated zirconias, siliceous zirconias, sulfated titanium oxides or tin oxides, phosphated aluminas or silicas, or tungstated or phosphotungstated titanium oxides or tin oxides.

Advantageously, use may also be made of a catalytic system comprising oxygen, iron, phosphorus, and one or more elements chosen from the alkali metals, the alkaline-earth metals, Al, Si, B, Co, Cr, Ni, V, Zn, Zr, Sn, Sb, Ag, Cu, Nb, Mo, Y, Mn, Pt, Rh, the rare earths La, Ce, Sm, or a catalytic system comprising oxygen, phosphorus and at least one metal chosen from vanadium, boron or aluminum.

These catalysts all have a Hammett acidity $H_0$ of less than +2, the $H_0$ acidity can then vary to a large extent, as far as values that may reach −20 in the reference scale with the Hammett indicators. The table given on page 71 of the publication on acid-base catalysis (C. Marcilly) vol. 1 in the Editions Technip (ISBN No. 2-7108-0841-2) illustrates examples of solid catalysts in this acidity range.

The overall reaction can be summarized by the following reaction mechanism, without however seeking to be bound to any theory:
(1) reaction for de-acetalization of the cyclic acetals (I) and (II):

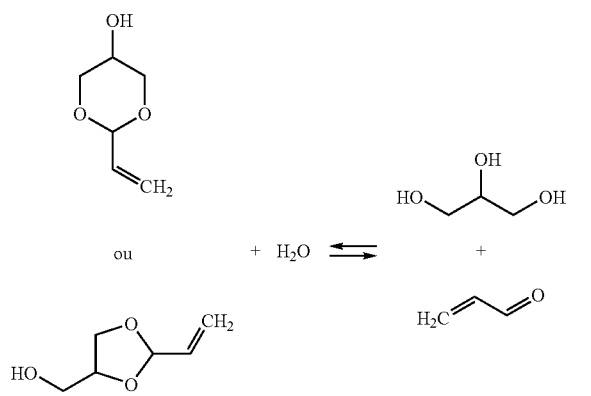

(2) reaction for dehydration of the glycerol so as to give acrolein

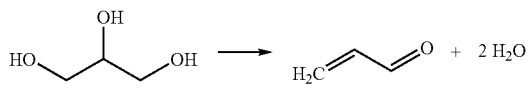

Advantageously, the reactor 6 can be supplied, at 3, with molecular oxygen, air, or a gas containing molecular oxygen.

The content of molecular oxygen introduced into the reaction medium may depend on the nature of the catalyst used, on its acidity and on its ability to form coke. Typically, oxygen is introduced at a content of between 0.1% and 25% by volume, and preferably between 0.1% and 10% by volume.

The temperature used to carry out reactions (1) and (2) described above is, as a general rule, between 180° C. and 350° C., preferably between 250° C. and 350° C.

In a fourth step (d) of the method according to the invention, the acrolein produced in the previous step (c) is recovered so as to be partly recycled to the first step (a).

Various methods (not represented in the FIGURE) can be used to separate the acrolein 4 from the reaction medium. In particular, a partial condensation of the water present with the acrolein and also of the heavy products formed during the dehydration step makes it possible to concentrate the gas stream with acrolein. The concentrated stream is then separated into 2 fractions, one being recycled to the first step (a) in order to supply the cyclic acetal production unit, and the other being directed downstream to the additional steps for purification of the acrolein or for conversion of the acrolein, for example into acrylic acid, acrylonitrile, methionine or other fine chemistry products.

An alternative to the partial condensation of the water and of the heavy products can be the total condensation of the products of the reaction followed by partial distillation of the acrolein produced. A part of the acrolein distilled is then recycled to the first step (a), the rest then being recovered.

The method according to the invention has many advantages in terms of energy consumption and yield. It may also comprise a step (e) of conversion of the acrolein produced, in a unit for producing acrylic acid, acrylonitrile, methionine or any other acrolein-derived product.

The invention also relates to the use of a mixture of cyclic acrolein glycerol acetals as an intermediate product for producing acrolein from aqueous solutions of glycerol in the gas phase.

The following examples illustrate the invention without, however, limiting the scope.

EXAMPLES

Example 1

Preparation of a Mixture of Cyclic Acrolein Glycerol Acetals

Example 1 of U.S. Pat. No. 5,216,179 is reproduced in order to obtain a mixture containing the cyclic acrolein glycerol acetals, unconverted acrolein and glycerol, and water. After fractionated distillation of the mixture, the conversion rates and the selectivities obtained are substantially identical to those expected.

Example 2

Preparation of a Mixture of Cyclic Acrolein Glycerol Acetals

Example 1 of U.S. Pat. No. 5,216,179 is reproduced, using a 4-liter fixed bed of Amberlyst 15 acidic resin in a loop reactor having a volume of 40 liters. This time, the composition of the reaction loop is 13% of acrolein, 55% of acrolein glycerol acetal, 22% of glycerol, 7% of water and 3% of by-products. The mixture is continuously fed into the circuit at a temperature of 15° C.

16.2 kg/h of glycerol and 9.9 kg/h of acrolein are continually fed into the loop reactor. Similarly, an equivalent volume of products is continually drawn off from the reactor. A mixture containing the cyclic acrolein glycerol acetals, unconverted acrolein and glycerol, water, and by-products is obtained. A fractionated distillation is carried out on the mixture without the pH being adjusted. The conversion rate for the acrolein added is 66% and that for the glycerol is 64%.

Example 3

Preparation of Acrolein

A bed of catalyst is charged to a pyrex reactor having a volume of 20 ml. The reactor is equipped with a frit in order to retain the catalyst. A mass of 7.2 g of a dehydration catalyst of tungstated zirconia type (Dailchi Kigenso KK, of reference Z1044), diluted with 7 ml of 0.062 mm silicon carbide, is first of all charged. The reactor is then made up with 2 ml of 0.125 mm silicon carbide, 2 ml of 0.5 mm silicon carbide, and, finally, 1.19 mm silicon carbide to the top of the reactor.

The reactor is then connected to the test plant. The temperature of the catalyst is regulated at 300° C.

The crude mixture, containing the cyclic acrolein glycerol acetals, obtained in example 2, is mixed with water in proportions of 1 kg/1 kg.

13 q/h of the aqueous mixture are then vaporized at 245° C., and then sent to the reactor in the form of a gaseous mixture of acetals/acrolein/glycerol/oxygen/helium-krypton/water, in the proportions 5.5/3/3.2/3.4/9.9/75(%). The helium-krypton gaseous mixture contains 4.92% of krypton, which serves as an internal standard.

The total hourly molar flow rate is adjusted so as to obtain an hourly space velocity (VVH) of 1600 h$^{-1}$.

These conditions represent a total composition of compounds in terms of glycerol equivalent (acetals glycerol) of 8.7%.

The effluents are collected at the reactor outlet using a cold ice trap, and the acrolein and the acrylic acid produced are assayed by chromatographic analysis.

The effluents are cumulated in the trap for a period of 60 minutes. The noncondensable gases are analyzed for the period of the analysis. The amount of acrolein collected is 4.1 g/h.

The acrolein yield is 70%, and there is complete conversion of the glycerol and of the glycerol acetals. The products of the previous reaction are then distilled, so as to produce the acrolein-water azeotrope which can be recycled.

The invention claimed is:

1. A method for producing acrolein from glycerol, comprising the following steps:
    (a) reacting, in a first reactor, an aqueous glycerol solution with acrolein in the presence of an acid catalyst so as to form cyclic acrolein glycerol acetals,
    (b) evaporating the stream derived from step (a) at a temperature of between 100° C. and 300° C.,
    (c) passing a gas stream obtained in step (b) over a glycerol dehydration catalyst in a second reactor, so as to produce an acrolein containing stream,
    (d) separating the acrolein from the acrolein containing stream derived from step (c), a part of the acrolein being recycled to the first reactor of step (a) for production of acetals.

2. The method as claimed in claim 1, characterized in that the aqueous glycerol solution has a concentration of at least 20% by weight.

3. The method as claimed in claim 1 or 2, characterized in that the reaction of step (a) is carried out with an acrolein/glycerol molar ratio ranging from 0.5 to 5.

4. The method as claimed in claim 1, characterized in that it further comprises a step of diluting the stream derived from step (a) before step (b).

5. The method as claimed in claim 1, characterized in that the temperature of step (b) is between 130° C. and 250° C.

6. The method as claimed in claim 1, characterized in that the dehydration catalyst of step (c) is a solid acid catalyst having a Hammett acidity $H_0$ of less than +2.

7. The method as claimed in claim 1, further comprising adding molecular oxygen or a gas containing molecular oxygen in step (c).

8. The method as claimed in claim 1, characterized in that step (d) is carried out by partial condensation of water and of heavy products formed during step (c).

9. The method as claimed in claim 1, characterized in that it further comprises a step (e) of converting the acrolein from step (d) into acrylic acid, acrylonitrile, or methionine.

10. A method for producing acrolein from aqueous solutions of glycerol, in the gas phase, wherein a mixture of cyclic acrolein glycerol acetals is an intermediate product.

* * * * *